(12) United States Patent
Thau et al.

(10) Patent No.: US 7,967,824 B2
(45) Date of Patent: Jun. 28, 2011

(54) BONE CUTTING FIXTURE ASSEMBLY WITH GUIDE APPENDAGES

(75) Inventors: Gary Thau, Morgantown, PA (US); Patrick White, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 1132 days.

(21) Appl. No.: 11/617,750

(22) Filed: Dec. 29, 2006

(65) Prior Publication Data

US 2007/0270872 A1    Nov. 22, 2007

Related U.S. Application Data

(60) Provisional application No. 60/747,686, filed on May 19, 2006.

(51) Int. Cl.
  *A61B 17/58* (2006.01)
  *A61B 17/60* (2006.01)
  *A61F 2/00* (2006.01)

(52) U.S. Cl. ..................................................... 606/88

(58) Field of Classification Search .............. 606/87–89, 606/96, 98
See application file for complete search history.

(56) References Cited

U.S. PATENT DOCUMENTS

| | | | |
|---|---|---|---|
| 4,074,431 A | 2/1978 | Beaver et al. | |
| 4,721,104 A | 1/1988 | Kaufman et al. | |
| 4,955,959 A | 9/1990 | Tompkins et al. | |
| 4,964,710 A | 10/1990 | Leiner | |
| 5,281,214 A | 1/1994 | Wilkins et al. | |
| 5,313,935 A | 5/1994 | Kortenbach et al. | |
| 5,342,396 A | 8/1994 | Cook | |
| 5,447,265 A | 9/1995 | Vidal et al. | |
| 5,454,815 A | 10/1995 | Geisser et al. | |
| 5,490,854 A | 2/1996 | Fisher et al. | |
| 5,509,923 A | 4/1996 | Middleman et al. | |
| 5,569,163 A | 10/1996 | Francis et al. | |
| 5,571,110 A | 11/1996 | Matsen, III et al. | |
| 5,683,397 A * | 11/1997 | Vendrely et al. | 606/88 |
| 5,817,097 A | 10/1998 | Howard et al. | |
| 5,925,049 A * | 7/1999 | Gustilo et al. | 606/82 |
| 6,120,508 A | 9/2000 | Gruenig et al. | |
| 6,602,259 B1 | 8/2003 | Masini | |
| 6,679,886 B2 | 1/2004 | Weikel et al. | |

(Continued)

FOREIGN PATENT DOCUMENTS

EP    0376657    7/1990

(Continued)

OTHER PUBLICATIONS

European Office Action for Application No. 07 734 595.7-1269 dated Sep. 29, 2010.

*Primary Examiner* — Thomas C Barrett
*Assistant Examiner* — Sameh Boles
(74) *Attorney, Agent, or Firm* — Michael F. Scalise

(57) ABSTRACT

A bone cutting fixture assembly for use as guide for a cutting blade in shaping a distal end of a femur to receive a component of a knee prosthesis is provided. The assembly has a centrally located, elongated support structure, made of a polymeric material, having a trapezoidal cross section, pairs of adjacent blade guide appendages supported therein so as to define four cutting planes, and two outrigger portions extending therefrom defining anchor points in distal ends thereof. The assembly defines a substantially flat support plane and has spaced apart anchor points positioned so as to enable secure fixing of the fixture to a femur by fixing devices.

27 Claims, 14 Drawing Sheets

U.S. PATENT DOCUMENTS

| | | |
|---|---|---|
| 6,702,821 B2 | 3/2004 | Bonutti |
| 6,869,392 B2 | 3/2005 | Dickopp et al. |
| 2001/0001120 A1 | 5/2001 | Masini |
| 2002/0165549 A1 | 11/2002 | Owusu-Akyaw |
| 2003/0018338 A1* | 1/2003 | Axelson et al. ............... 606/89 |
| 2004/0138670 A1* | 7/2004 | Metzger ........................ 606/88 |
| 2004/0260301 A1 | 12/2004 | Lionberger et al. |
| 2005/0240196 A1 | 10/2005 | Davis et al. |
| 2006/0111725 A1 | 5/2006 | Biegun |

FOREIGN PATENT DOCUMENTS

| | | |
|---|---|---|
| EP | 0376657 | 10/1993 |
| EP | 0 574 701 | 12/1993 |
| EP | 0 581 400 | 2/1994 |
| EP | 0655224 | 5/1995 |
| EP | 0 965 307 | 12/1999 |
| FR | 2 600 530 | 12/1987 |
| FR | 2 847 453 | 5/2004 |
| JP | 2004147724 | 5/2004 |
| WO | WO 91/02493 | 3/1991 |
| WO | WO 94/20247 | 9/1994 |
| WO | WO 98/37819 | 9/1998 |
| WO | 9853747 | 12/1998 |
| WO | WO 99/65403 | 12/1999 |
| WO | WO 02/087422 | 11/2002 |
| WO | WO 2004/032806 | 4/2004 |
| WO | WO 2004/047655 | 6/2004 |
| WO | WO 2005/084558 | 9/2005 |

* cited by examiner

BONE CUTTING FIXTURE ASSEMBLY WITH GUIDE APPENDAGES

CROSS REFERENCE TO RELATED APPLICATIONS

This application claims priority under the Paris Convention to U.S. patent application Ser. No. 60/747,686, filed May 19, 2006, the content of which is incorporated herein by reference thereto.

BACKGROUND OF THE INVENTION

This invention relates to surgical cutting guides, and in particular to a guide for a cutting blade in shaping a distal end of a femur to receive a component of a knee prosthesis.

U.S. Pat. No. 6,702,821 to Bonutti, entitled "Instrumentation for minimally invasive joint replacement and methods for using same", describes a method of performing surgery on a joint in a patient's body using a cutting guide. During cutting of the bone, a surgical cutting guide having guide members with opposite ends spaced apart by a distance less than the width of an implant may be utilized. This patent contemplates making the guide out of inexpensive, light weight material such as polymeric materials.

U.S. Pat. No. 4,721,104 to Kaufman entitled "Femoral Surface Shaping Apparatus for Posterior-stabilized Knee Implants", describes a surgical cutting guide including (a) a template having (1) a bottom surface which is adapted to be placed in an aligning relationship with the flat surface of a distal femur which has been partially shaped to receive the femoral component of a posterior-stablized knee implant prosthesis and (2) a U-shaped slot passing through the template where the slot is of substantially the same size and shape as the outer periphery of the intercondylar stabilizing housing present on the femoral component to be implanted and (b) a drilling means, preferably in the form of an end-mill cutter, having a stop means thereon and the drilling means closely engages the sides of the U-shaped slot in the template so that the drilling mean can be passed through the U-shaped slot until the stop means contacts a surface of the guide and is then drawn along the slot to create a precisely shaped and aligned recess in the femur for receipt of the intercondylar stabilizing housing. It is contemplated that at least a portion of the guide be made of plastic.

U.S. Pat. No. 6,602,259 to Masini, entitled "Bone cutting guides for use in the implantation of prosthetic joint components" and U.S. Patent application Publication No. 2001001120, also to Masini, entitled "Apparatus and method for preparing box cuts in a distal femur with a cutting guide attached to an intramedullary stem", describe cutting guides enabling a surgeon to gauge required resection characteristics. It is contemplated to make the guide at least in part from plastic, in particular, polyethylene. In the later mentioned Masini application, the plastic is transparent to enable better visibility of the bone during cutting.

U.S. Pat. No. 5,490,854 to Fisher, entitled "Surgical cutting block and method of use" describes an improved surgical cutting block for guiding bone saws in joint surgery and similar instruments which may also be fabricated from polyethylene plastics.

U.S. Patent Application Publication No. 2006011725 to Biegun, entitled "Accessories for removing bone material and method for making same" concerns a surgical cutting guide in part made of a material harder than the bone material to be cut, as well as plastic material.

U.S. Patent Publication No. 200400260301 to Lionberger, entitled "Cutting guide apparatus and surgical method for use in knee arthroplasty" describes cutting guides and surgical methods for use in knee arthroplasty which are made at least in part by plastic, thus providing for an economical, single-use application.

All of the above references describe guides which include a massive housing which covers the head of the femur and may obstruct view of the bone during cutting. Even the latter Masini device which is transparent may obstruct the view of the bone during cutting when the plastic is covered with body fluids or where refraction of light may distort such view.

An effort to minimize this obstruction is apparent in U.S. Pat. No. 5,817,097 to Howard et al. entitled "Bone Saw with Magnet". Howard's magnet exerts attractive force in a direction toward the guide body for attracting a bone saw blade or milling instrument to the guiding surface. However, questions may be raised of the secure guiding of the cutting blade when there is no tangible surface to restrict movement of the cutting tool. Further, the strong magnet may have disruptive effects on instruments that are sensitive to magnet fields.

What is needed is a surgical cutting guide for the multiple cuts associated with preparation of the femur for reception of a prosthesis in a manner that minimizes obstruction of the cut surfaces. Further, what is needed is a surgical cutting guide that is light weight, inexpensive and disposable.

Nothing herein is to be construed as an admission that the present invention is not entitled to antedate such material by virtue of prior invention.

SUMMARY OF THE INVENTION

A bone cutting fixture assembly for use as guide for a cutting blade in shaping a bone to receive a component of a knee prosthesis is provided. The assembly has a centrally located, elongated support structure, made of a polymeric material, having a trapezoidal cross section, pairs of adjacent blade guide appendages supported therein so as to define four cutting planes, and two outrigger portions extending therefrom defining anchor points in distal ends thereof. The assembly defines a substantially flat support plane and has spaced apart anchor points positioned so as to enable secure fixing of the fixture to a femur by fixing devices.

An object of the invention is to provide a surgical cutting guide for the multiple cuts associated with preparation of the femur and/or the tibia for reception of a prosthesis in a manner that minimizes obstruction of the cut surfaces.

Another object of the invention is to provide a surgical cutting guide that is light weight, inexpensive and disposable.

DETAILED DESCRIPTION OF THE PREFERRED EMBODIMENT(S)

Figure 1:
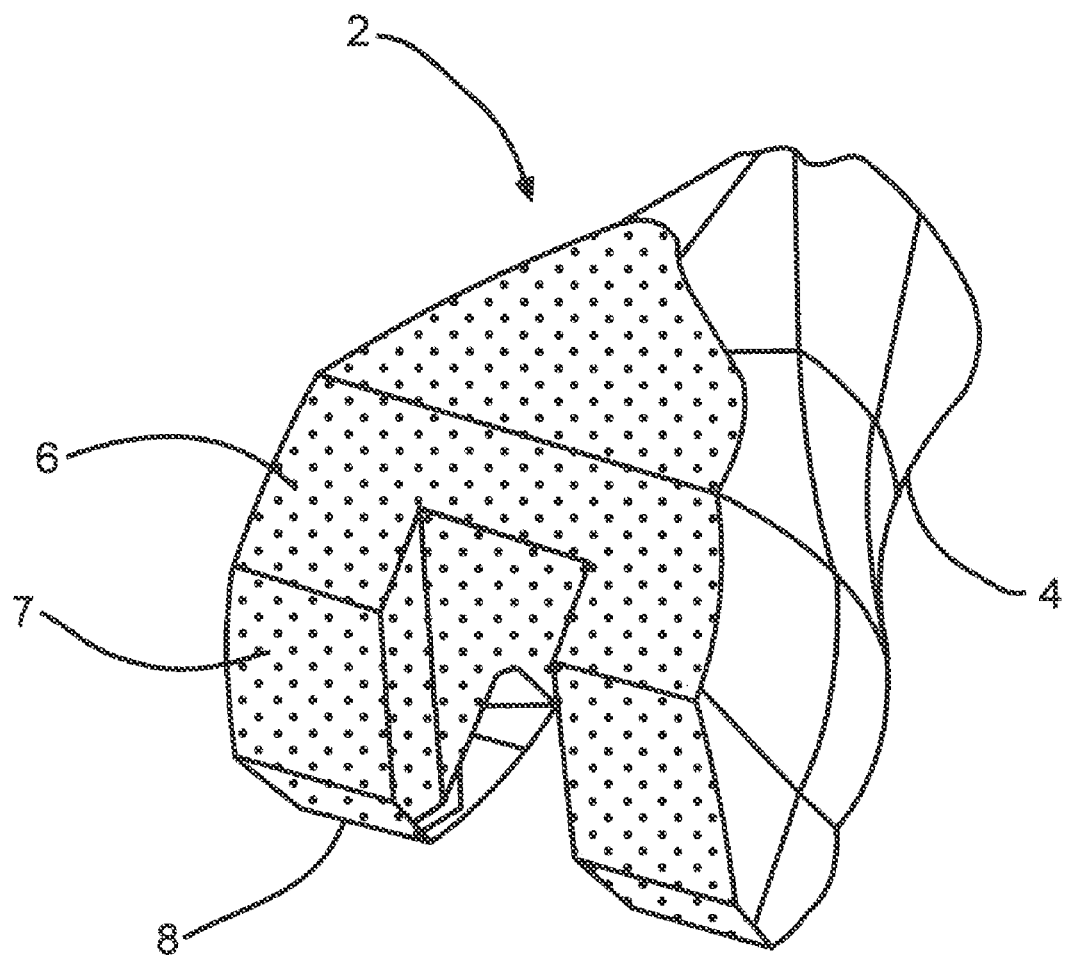
FIG. 1 is a perspective view of a femoral head, cut and ready to receive a prosthesis.

Referring now to the drawings, the details of preferred embodiments of the present invention are graphically and schematically illustrated. Like elements in the drawings are represented by like numbers, and any similar elements are represented by like numbers with a different lower case letter suffix.

Referring now to FIG. 1, during the preparation of the distal end 2 of the femur bone 4 to receive a knee prosthesis (not shown), a number of cuts 6, 7, and 8 must be made to properly shape the bone end. The present invention is a bone cutting fixture assembly 10, 10a with guide appendages 14, which is anchored to a flat-cut surface 16 on the distal end 2 of the femur bone. Once anchored, the cutting fixture assembly 10 is used for controlling and guiding a saw blade 34 when making one or more of the additional cuts required for shaping the femur bone distal end to receive a knee prosthesis.

Figure 2:
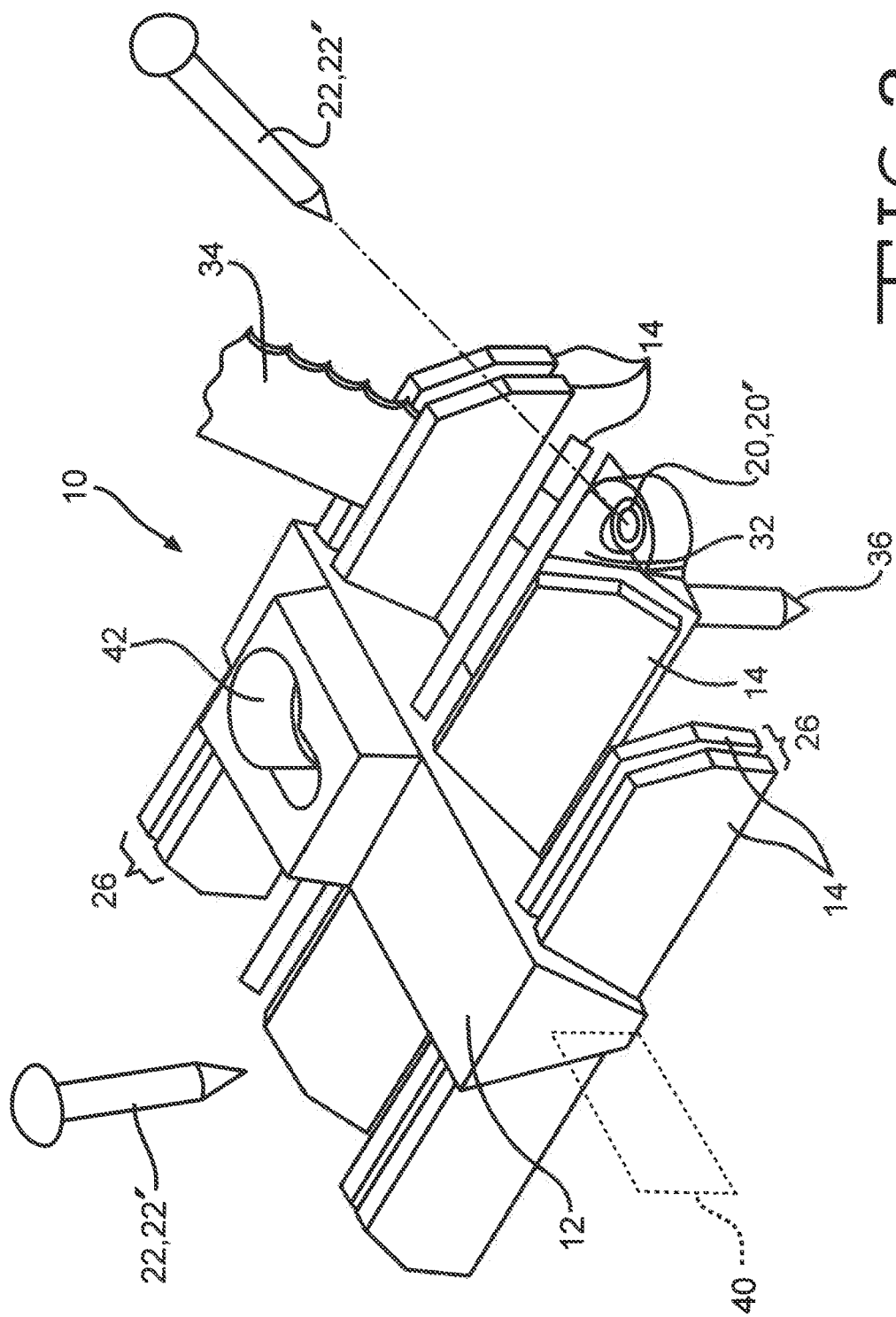
FIG. 2 is a perspective view of the cutting guide of the invention.
Figure 3:
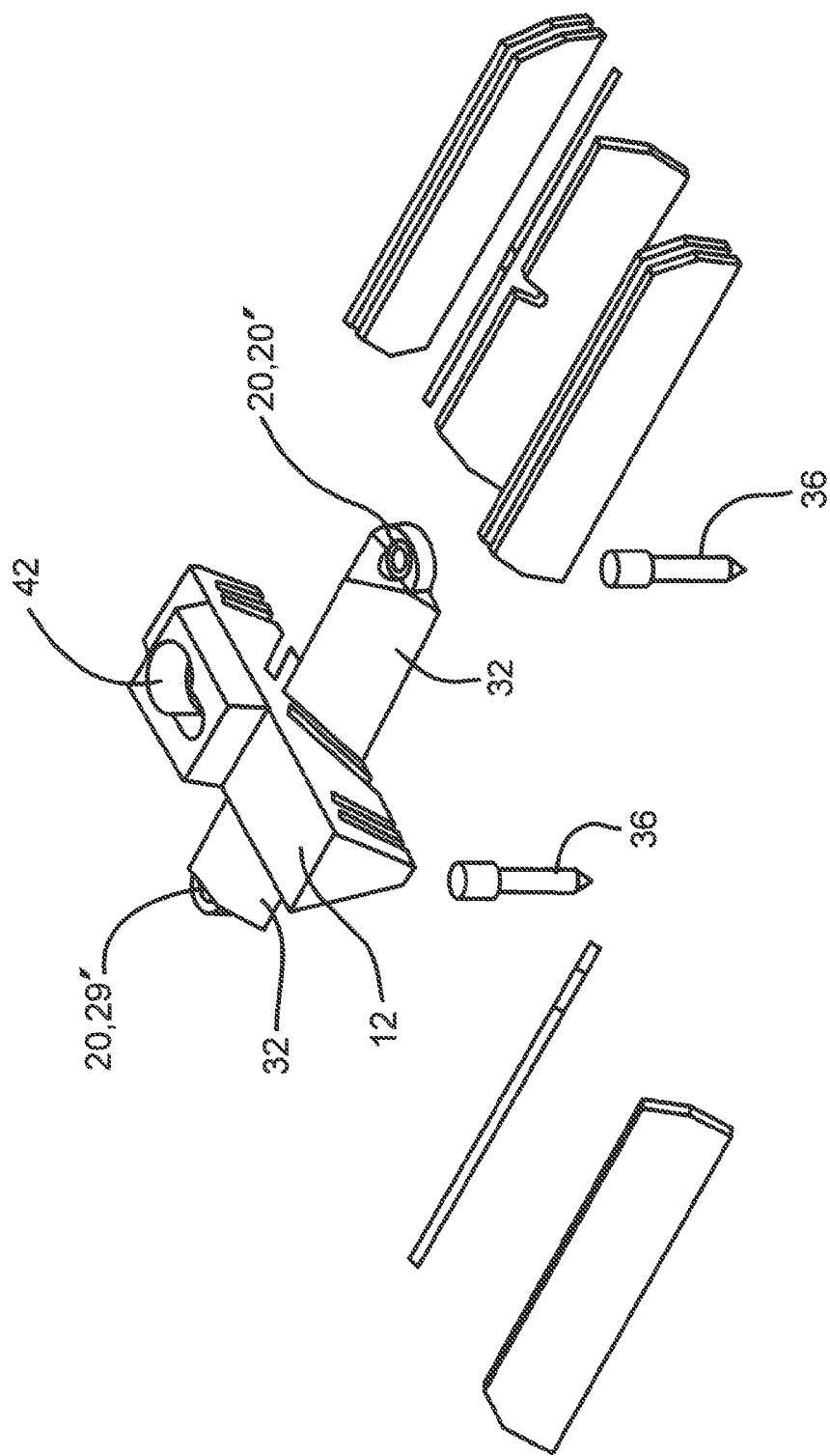
FIG. 3 is an exploded view of the cutting guide of the invention.
Figure 4:
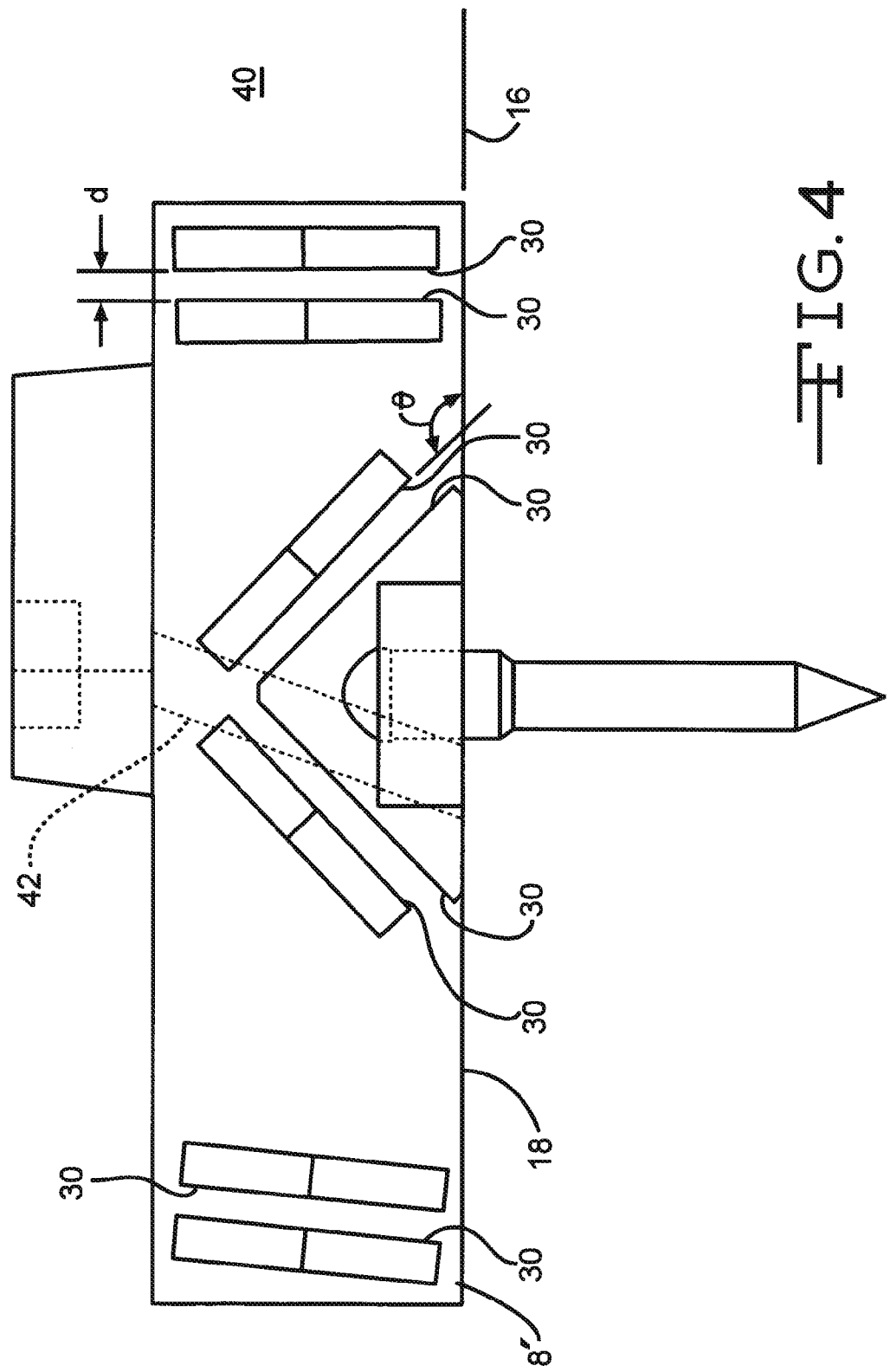
FIG. 4 is side view of the cutting guide of the invention.

Referring now to FIG. 2, a first embodiment of a bone cutting fixture assembly 10 has an elongated support structure 12 of polygonal, and in particular, trapezoidal cross section and preferably made of polymeric material. Guide appendages 14 are supported by the support structure 12. The assembly 10 defines a substantially flat support plane 16 (see FIG. 4) and has spaced apart anchor points 20 positioned so as to enable secure fixing of the fixture assembly 10 to the femur 4 by fixing devices 22, 22'.

In this embodiment, matched adjacent appendages 26 define eight adjacent guide surfaces 30. The surfaces 30 are formed on the guide appendages 26 and on outrigger portions 32 fixed to the elongated support structure 12 in an orientation so as to guide a cutting blade 34 therebetween and to restrict movement of cutting blades to within four cutting planes located between adjacent guide appendages 26. The outrigger portions 32 have fixed bone spikes 36 projecting therefrom, one on each side of a central plane 40 perpendicular to the flat support plane 16. The spikes 36 extend in a downward direction sufficiently beyond the flat support plane 16 of the cutting fixture 10 to function as bone anchors. The outrigger portions 32 also have a through bore 20' on a distal end, adjacent each bone anchor 36 and located proximate each end of the outrigger portions, with the through bores disposed so that a removable bone spike 22' is downwardly receivable in the bore at an angle from the perpendicular plane.

The pairs 26 of guide surfaces 30 are positioned at a defined angle $\theta$, $\theta'$ with respect to the flat support plane 16 and separated by a distance d sufficient to allow a thickness of a cutting blade 34 to closely pass between them.

In this first embodiment, the elongated support structure 12 is centrally located to the appendages 14 and at least two outrigger portions 32 are integral therewith and extend therefrom, to opposing anchor points 20. The elongated support structure 12 and the outrigger portions 32 are preferably molded of plastic as a unit. Further, the fixture 10 has an anchor point 42 at its center. Pairs 26 of adjacent appendages 14 are fixed to the elongated support portion 12 so as to guide a cutting blade therebetween.

Figure 5:
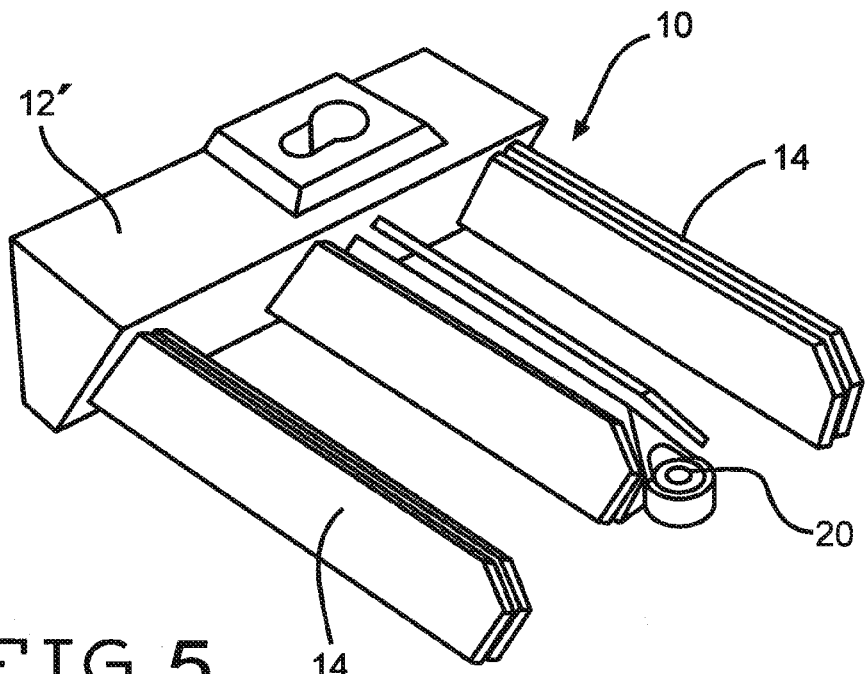
FIG. 5 is a perspective view of an alternate embodiment of the invention.

Referring now to FIG. 5, in an alternate embodiment, the elongated support structure 12 is located at an extreme end of the fixture 10, and the appendages 14 extend from one side thereof.

Figure 6:
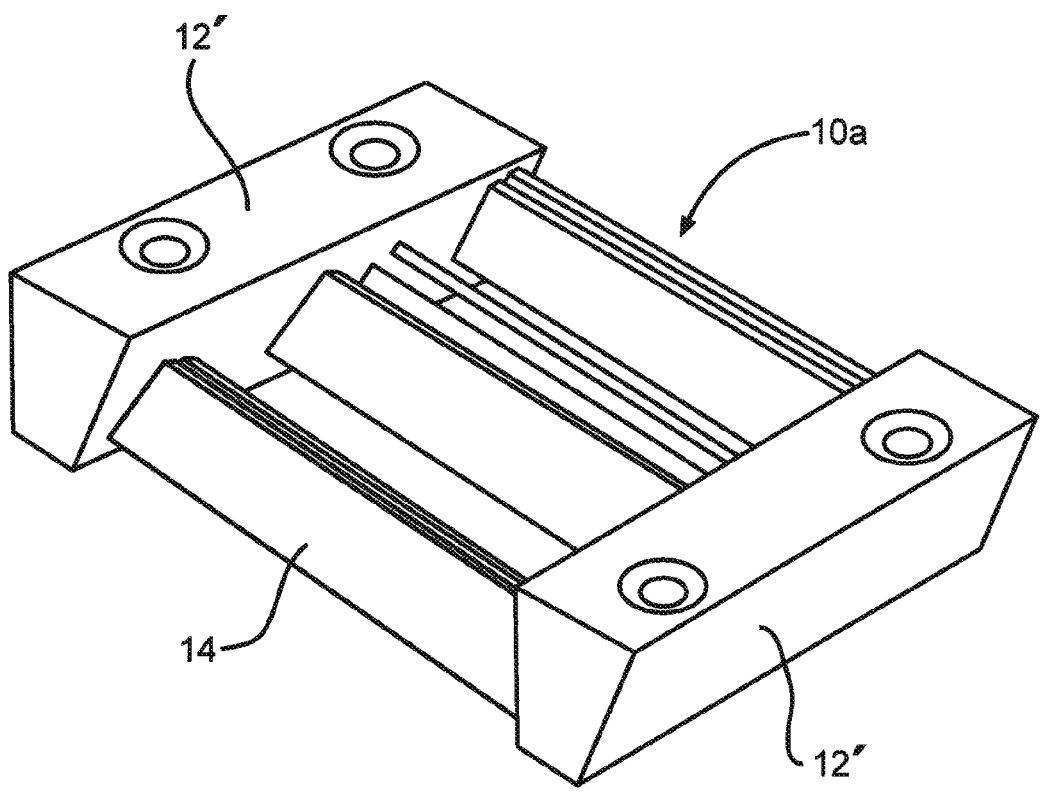
FIG. 6 is a perspective view of a second alternate embodiment of the invention.

Referring now to FIG. 6, in another alternate embodiment, two elongated support structures 12' are located at extreme ends of the fixture 10a, the appendages 14 extending therebetween. The adjacent appendages 14 define parallel flat guide surfaces 30 which guide the bone saw 34 in a single plane. The appendages 14 are slidable relative to at least one elongated support structure.

In order to restrain the cutting blade 34, at least two pairs of guide surfaces 30 are positioned at a defined orientation with respect to the flat support plane and separated by a distance suitable for guiding a thin cutting blade to closely pass therebetween.

Figure 7A:
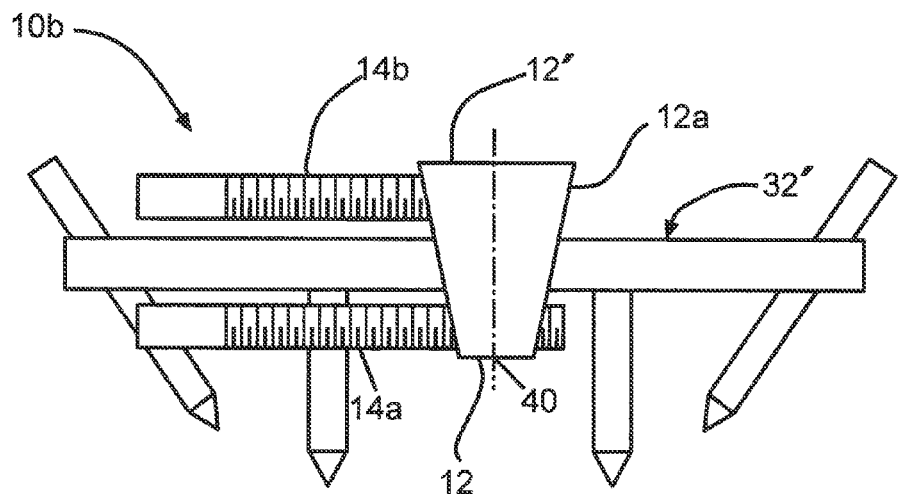
FIG. 7A is a perspective view of the distal end of a femur bone shaped by cutting in preparation for receiving a component of a knee-joint prosthesis.

Referring now to FIG. 7A, the present bone cutting fixture assembly 10b comprises an elongated support structure 12' having outrigger portions 32' mounted thereto, and the elongated support structure 12 further having a plurality of guide appendages 14a passing perpendicularly through a vertical plane 40 of the elongated support structure 12. The present bone cutting fixture assembly 10a is to be used as a guide for a cutting blade 34 when shaping the distal end 2 of a femur 4 to receive a component of a knee prosthesis. The cutting fixture assembly 10a comprises an elongated support structure 12 having a substantially flat bottom 18, a trapezoidal cross section and a vertical plane 40 perpendicular to the flat bottom 18. The vertical plane is defined along a length L of the elongated support structure 12. In the preferred embodiment illustrated, the elongated support structure 12 is made of a bio-compatible material, and preferably is resistant to abrasion by the action of the cutting blade 34.

In this embodiment, adjacent appendages 14a define sets of four proximate, ordered adjacent cylindrical surfaces which are adapted to restrict movement of a cutting blade to within a single cutting plane.

Figure 7B:
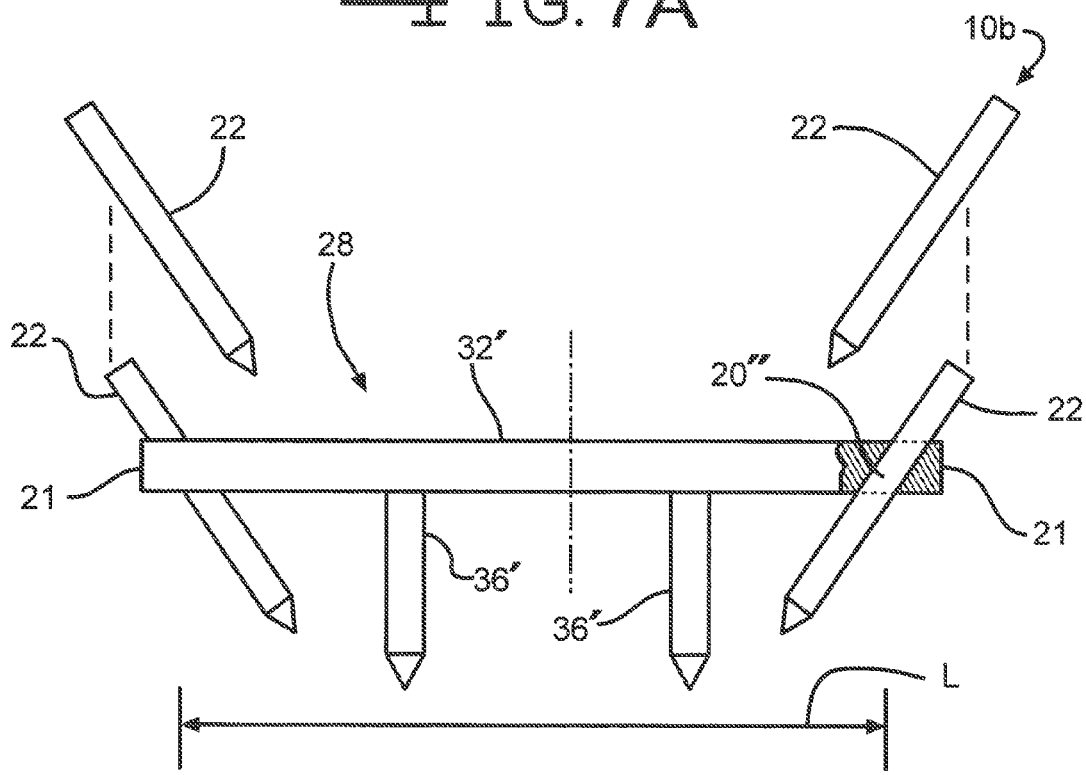
FIGS. 7B and 7C are end views of examples of the present bone cutting fixture assembly having (A) adjustable guide pines, and alternatively (B) having set guide pins.

Referring now to FIG. 7B, a preferred embodiment of the present bone cutting fixture assembly 10b is shown. In this embodiment, the outrigger portion 32' in the form of a mounting rod, extends through the elongated support structure 12. The outrigger portion 32' passes for about half its length l through the elongated support structure 12' perpendicular to the vertical plane 40. Placement of the outrigger portions 32' relative to certain of the guide appendages 14a is a feature of the present bone cutting fixture assembly 10b. Specifically, it is the placement of the outrigger portions 32' which dispose them to additionally serve in combination with certain of the guide appendages 14a as a cutting blade guide.

The outrigger portion 32' has two fixed bone spikes 36' projecting from the outrigger portions, one on each side of the vertical plane 40 in a downward direction sufficiently beyond the flat bottom 18 of the elongated support structure 12 to function as a bone anchor. The fixed bone spikes 36' protrude from the outrigger portions 32' perpendicular to its length l. The fixed bone spikes 36' are used to anchor the bone cutting fixture assembly 10b to the flat-cut surface 8 at the distal end 2 of the femur bone 4.

In this embodiment, the outrigger portions 32' also has a through spike bore 20" located proximate each end 21. The through bores 20" are disposed so that a removable bone spike 22 is receivable in the bore 20", and when received is angled toward the vertical plane 40. In use, the removable spikes 22 closely passed through spike bores 20" disposed proximate the rod ends 21 of the outrigger portions 32'. The spike bores 20" are canted at an oblique angle relative to the length l of the outrigger portions 32'. The removable bone spikes 22 are installed into the bone after the cutting fixture assembly 10b has been anchored using the fixed bones spikes 36'. The removable bone spikes 22 are used to further secure the anchoring of the cutting fixture assembly 10b to the bone surface 8, if additional security is needed.

Figure 12:
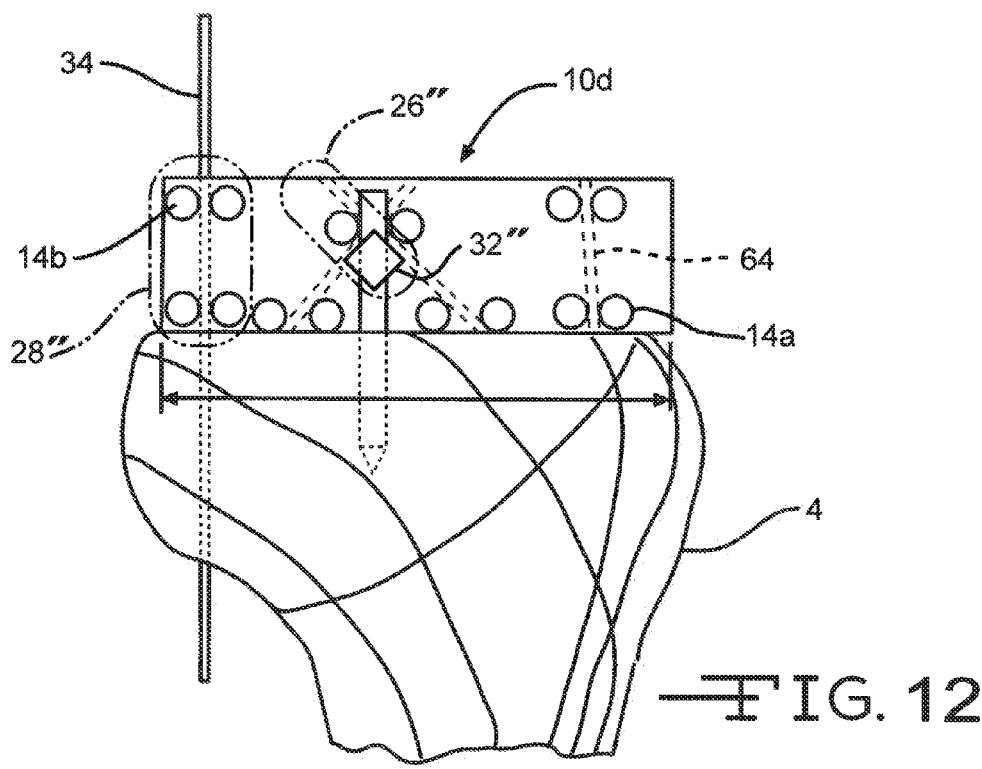
FIG. 12 is a side view of a cutting fixture assembly having bracket mounted guide pins at one end of the cutting fixture and fixture mounted guide pins at the other end.
Figure 13:
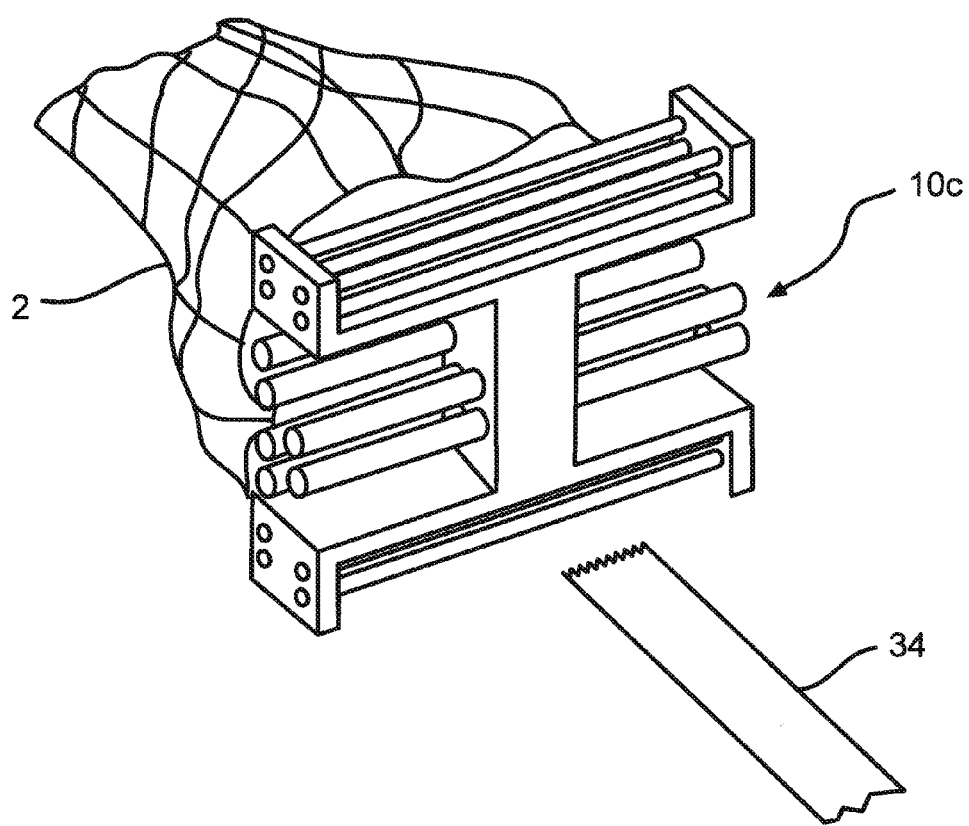
FIG. 13 is a perspective view of the cutting fixture of FIGS. 11A-11B.

Although the outrigger portions 32' in a preferred embodiment having a circular cross-section (e.g., see FIG. 8A), it can have alternative geometric cross-sections as well, which alternative cross-sections are selectable by one of reasonable skill in the art for practice in the present invention. For example, an outrigger portion 32" with a square cross-section is illustrated in FIG. 12.

After making a distal end cut (shown removed from the bone), the surgeon places the guide on the cut distal surface 8 of the femur 4. The fixed bone spikes 36' are then forced into the bone, and following that, the removable bone spikes 22 would be inserted into the bone.

In the embodiment shown in FIGS. 8A to 10, a plurality guide appendages 14a project from at least one side 12a of the elongated support structure 12, perpendicular to the vertical plane 40. The guide appendages 14a are arranged in a specific pattern in pairs 26', see FIG. 8A. The guide appendages 14a of an appendage pair 26' are separated by a distance d sufficient to allow the thickness of a cutting blade 34 to closely pass at an angle θ between them. The angle θ is defined as the angle between the bottom surface 18 of the support structure 12 and the length of the cutting blade 34 as it passes between a first pair 26' and a second pair 26' of appendages 14a, see FIG. 8B. The combination of the first and second appendage pairs 26' forms a guide appendage set 28 which limits the cutting path of the blade 34 to the angular path between the appendage pairs 26' of a set 28 (see FIG. 8B).

Figure 8A:
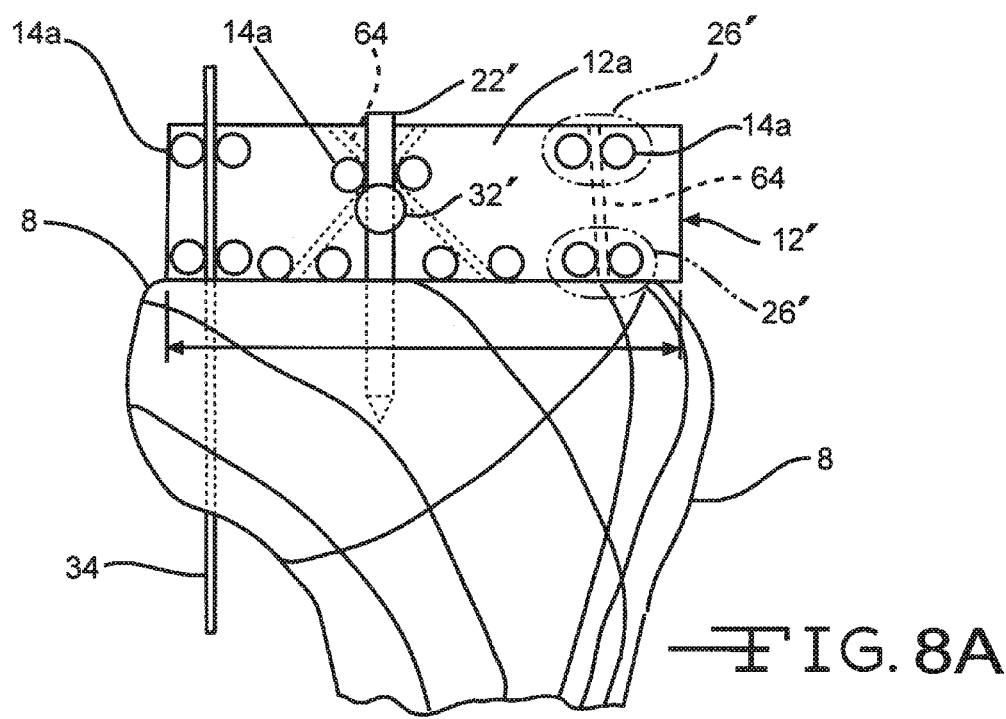
FIGS. 8A and 8B are side views of the present bone cutting fixture assembly mounted on a flat-cut surface of the distal end of a femur bone showing the relationship of the saw blade with different sets of guide pins.
Figure 8B:
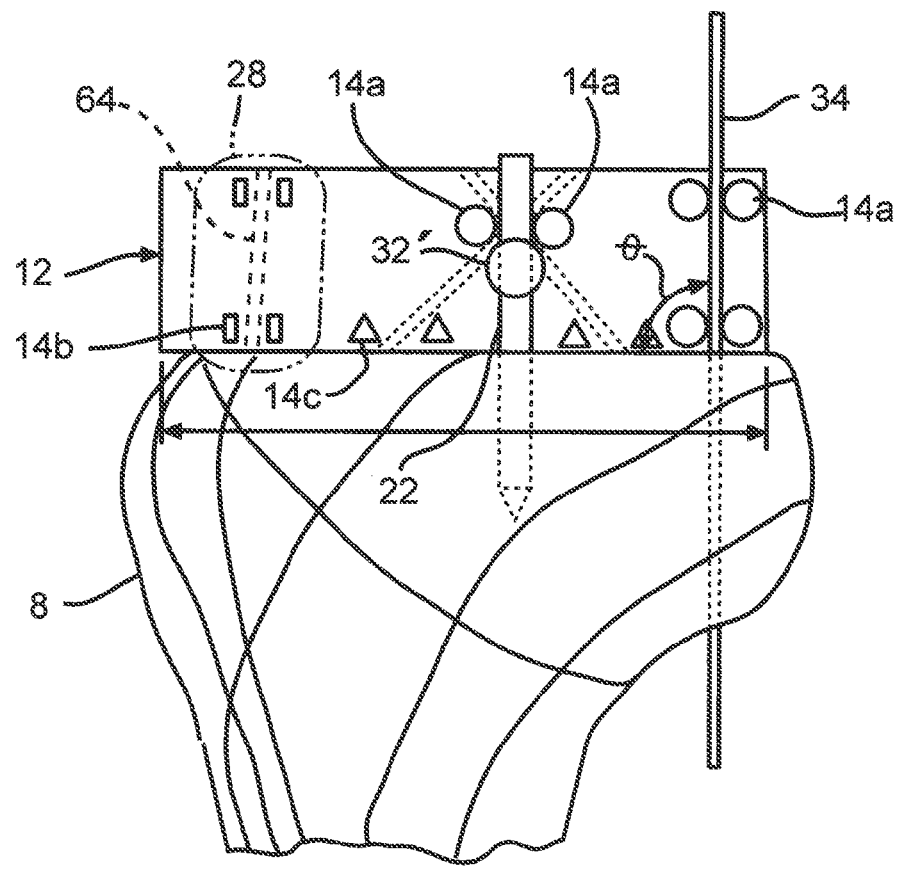
Figure 9:
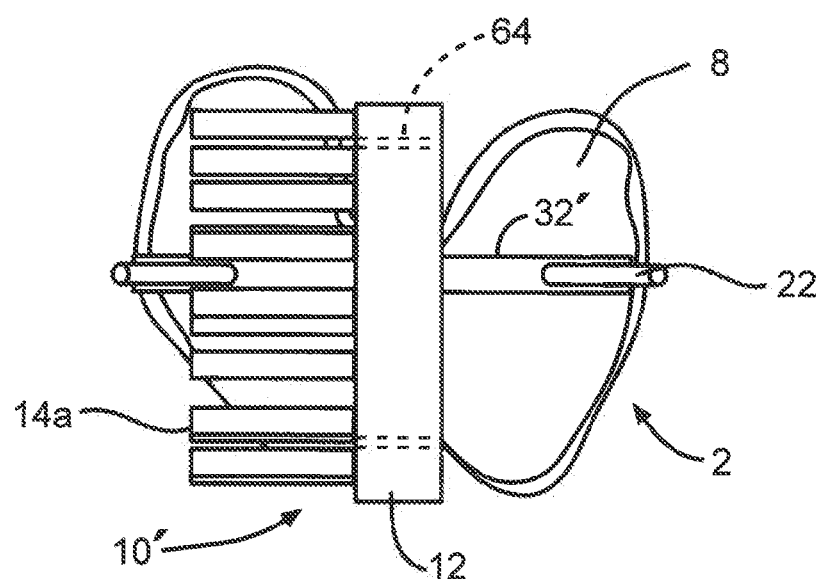
FIG. 9 is a top view of the present bone cutting fixture assembly having adjustable guide pins. The cutting fixture assembly is mounted on a flat-cut surface of the distal end of a femur bone.
Figure 10:
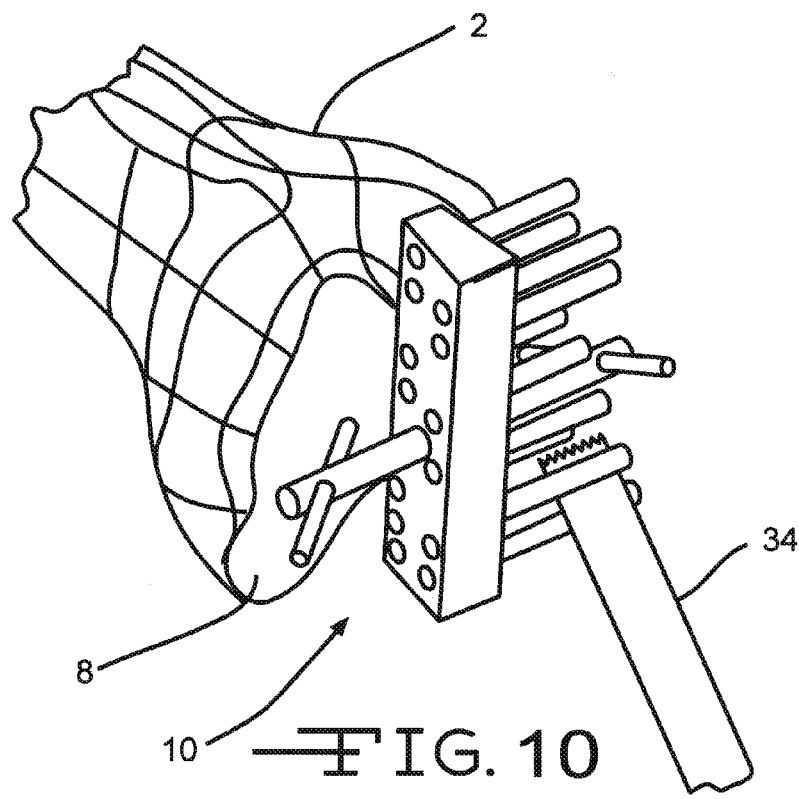
FIG. 10 is a perspective view of the bone cutting fixture assembly of FIG. 9 mounted on a flat-cut surface of the distal end of a femur bone, and illustrates the relationship of a saw blade with the guide pins of the cutting fixture.

Optionally, the bone cutting fixture assembly 10, 10a includes guide marks 64, such as the hash marks shown in FIGS. 8A, 8B and 9. The guide marks 64 indicate the insertion point and angle θ at which a cutting blade 34 is to be inserted into the assembly 10, 10a. This feature can facilitate installation and use of the cutting fixture assembly 10, 10a.

In preparation for using the assembly 10a, the surgeon makes a distal cut (shown removed) across the distal end 2 of the femur 4. Then the surgeon places the guide assembly 10a on the cut distal surface 8. The fixed spikes 36' of the anchor mechanism 32' are forced into the bone and then the obliquely angled removable spikes 22 as well. In the embodiment illustrated in FIG. 7A, the guide appendages 14a are threaded pins, which can be selectively set on one side 12a or the other of the elongated support structure 12. In the example shown, they are set on the medial side of the elongated support structure 12. The surgeon would perform the cuts between each set 28 of guide appendages 14a. The surgeon can tell from the guide mark 64 for an appendage set 28 where the centerline is between the guide appendages 14a to aid in placement of the cutting blade 34 between the guides 14a. The guide appendages 14a can be colored or otherwise differentiated to simplify use of the assembly 10a.

After making the cuts on the medial side, the surgeon would advance the threaded guide appendage pins 14a to the other side 12a of the guide fixture 12. Although the adjustable guide appendages 14a illustrated are threaded into the elongated support structure 12, other means of providing a side-to-side adjustable guide appendage 14a are intended as well. For example, the adjustable guides appendages 14a can incorporate a detent mechanism (as is known in the art) and so be snapped into the elongated support structure 12, or any other means of fixation that allows the guide appendages 14a to be translated from one side of the fixture to the other. Once the adjustable guide appendages 14a have been advanced to the opposite side of the elongated support structure 12, the surgeon can complete the complementary cuts to the distal end 2 of the femur 4. In addition to having a circular cross-section, the guide appendages can have other cross-sectional configurations as well, such as the flat guide appendage 14b and the angle guide appendage 14c of FIG. 8B.

An advantage of the assembly 10, 10a with adjustable guide appendages 14, 14a, and 14c is to allow a better view of the cutting plane than can be had with other cutting guides have larger bodies or cutting slots with additional material that fixtures the view of the surface being cut. Also, this embodiment includes the benefit of being able to adjust/translate the guide appendages 58 to allow for a smaller instrument foot print than similar cut guides that exist for use in MIS approaches. Additionally, in the preferred embodiment, the elongated support structure 12 is made of a clear polymer to further improve the ability to view the cutting surface.

It should be noted that the outrigger portions 32 can function as a guide appendage 14 when appropriately combined with a guide appendage 14a dedicated to that function to from an appendage guide pair 26" (see FIG. 12).

Figure 7C:
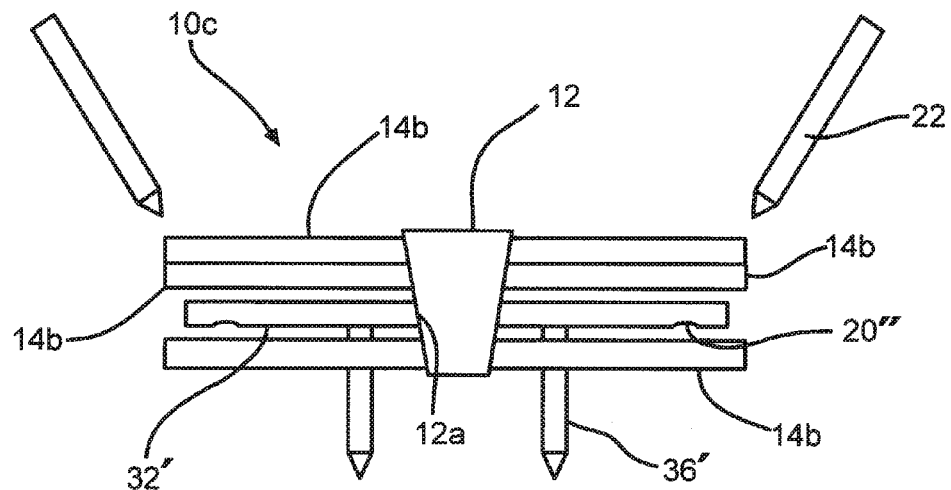

In another preferred embodiment shown in FIG. 7C, the bone cutting fixture assembly 10c has full length guide appendages 14b that protrudes from both sides 12a of the elongated support structure 12, perpendicular to the vertical plane 40. These full length guide appendages 14b can be fixed in place or can be removable in the manner of the adjustable guide appendages 14a. The use of this embodiment does not require the translation of the guide appendages 14b from one side 12a of the elongated support structure 12 to the other. After making the cuts on the medial side, the surgeon would make the cuts of the lateral side of the bone, though either side can be cut before the other.

Figure 11A:
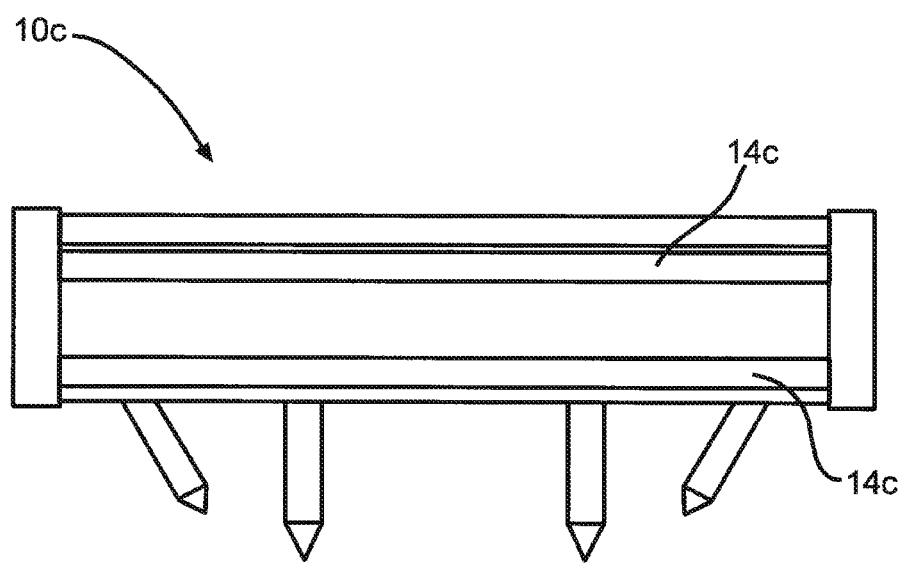
FIG. 11A is an end view of an alternative bone cutting fixture assembly where the guide pins at the fixture end shown are mounted at both ends in a bracket assembly.
Figure 11B:
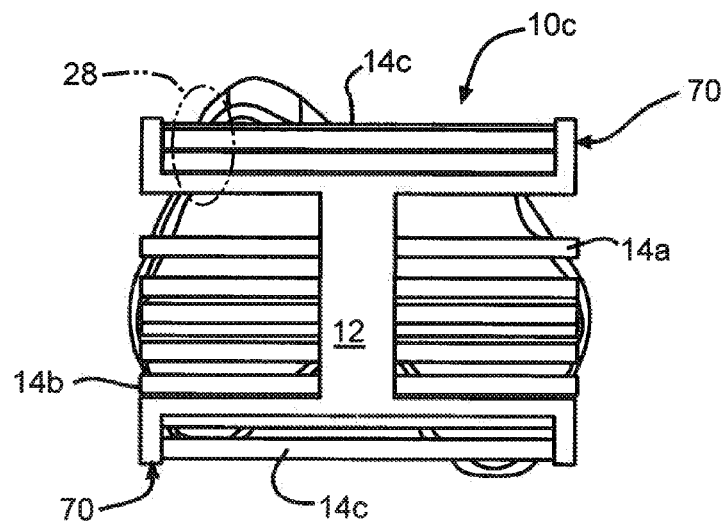
FIG. 11B is a top view showing bracket mounted guide pins a both end of the cutting fixture (A), and the relationship of a saw blade with the end mounted guide pins of the cutting fixture (B).

In still another preferred embodiment shown in FIGS. 11A and 11B, the bone cutting fixture assembly 10c has guide appendages 14c that at least some of the guide appendages disposed in a trap assembly 70. In the embodiment illustrated, the guide appendage sets 28a for making the anterior and posterior cuts are closed at each end laterally and medially, which aids the surgeon in controlling the cutting blade 34. The closed-ended "slots" of the trapped guide appendages 14c can simplify the use of the assembly 10c in that the surgeon will be prevented from extending a cut outside of the guide appendages 14c as easily as with an open guide appendage set 28. The more centrally disposed guide appendages 14b are illustrated as full length, but could be the adjustable-type as well.

In another preferred embodiment, an alternate bone cutting fixture assembly (not shown) is a combination of the assemblies 10b and 10c. In this embodiment, only the appendage set 28c at one end of the cutting fixture has the Guide appendages 58c being of the "trapped" type.

Figure 14A:
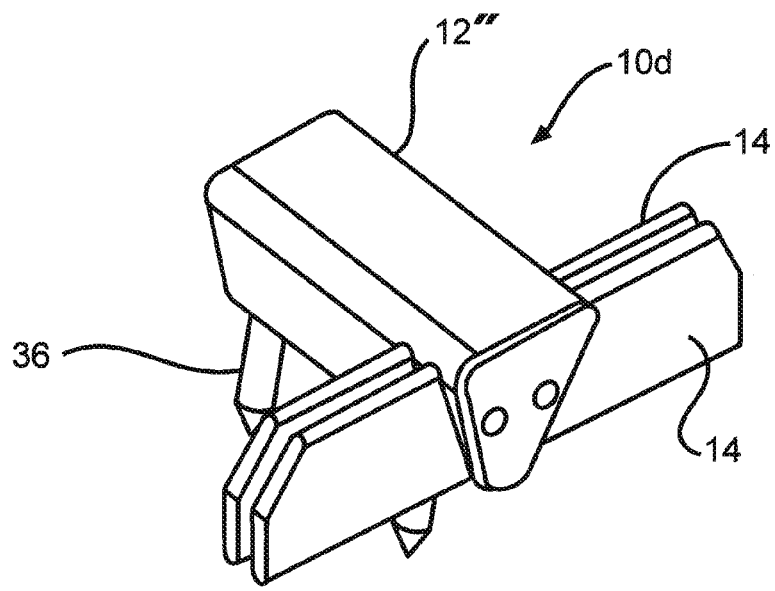
FIG. 14A is a perspective view of a simplified, alternate embodiment of a distal femoral cutting guide of the invention.
Figure 14B:
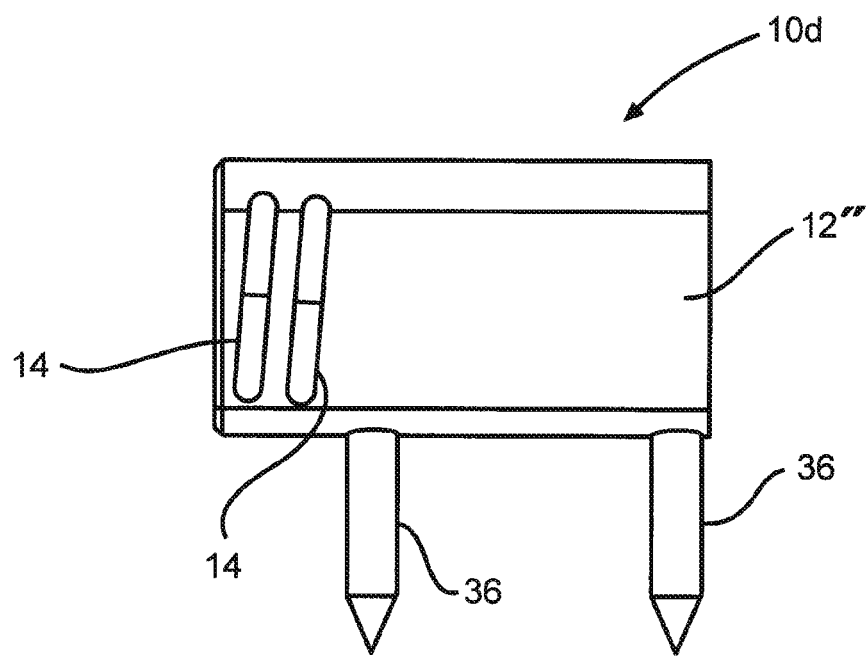
FIG. 14B is a side view of the alternate embodiment of FIG. 14A.

Referring now to FIGS. 14A and 14B, a simpler embodiment of the bone cutting fixture assembly 10d is very similar to the embodiments shown in FIGS. 2 to 6, except that only one pair of appendages 14 is optionally slidably installed in the support structure 12". This embodiment is suitable for use as a distal femoral cutting guide.

Figure 15A:
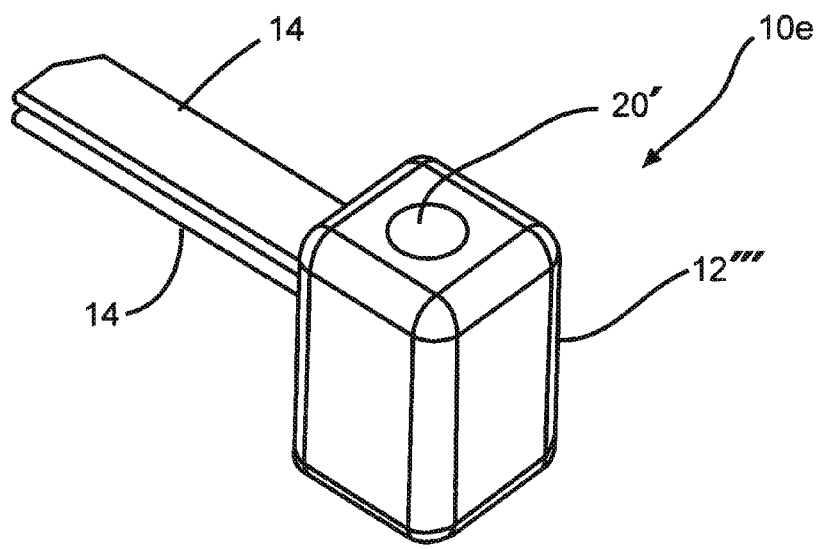
FIG. 15A is a perspective view of a further simplified alternate embodiment of a tibial cutting guide of the invention.
Figure 15B:
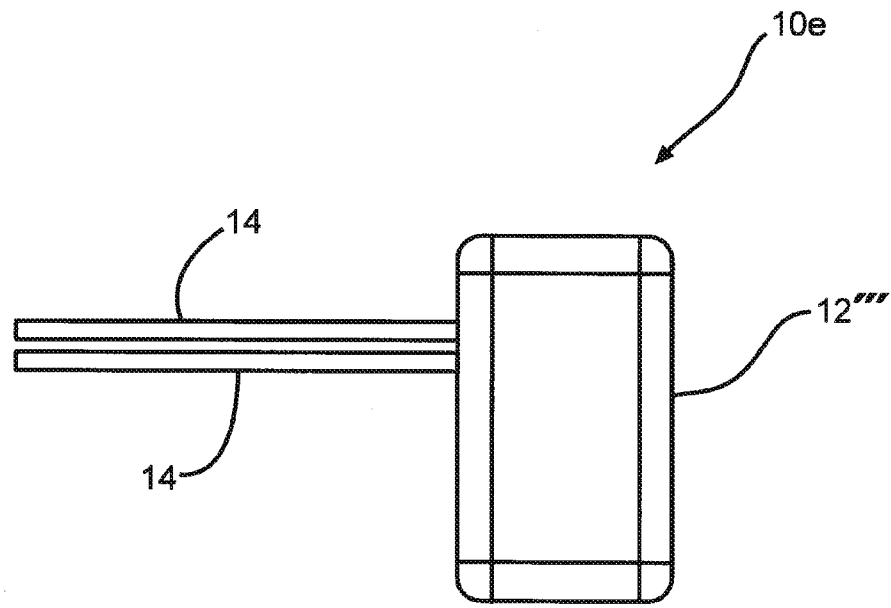
FIG. 15B is a side view of the alternate embodiment of FIG. 15A.

Referring now to FIGS. 15A and 15B, a still simpler embodiment of the assembly 10e is shown, in which the appendages 14 are affixed to a support structure 12''' which is essentially a standoff with an alignment guide hole. This embodiment is suitable for use as a tibial cutting guide.

Figure 16:
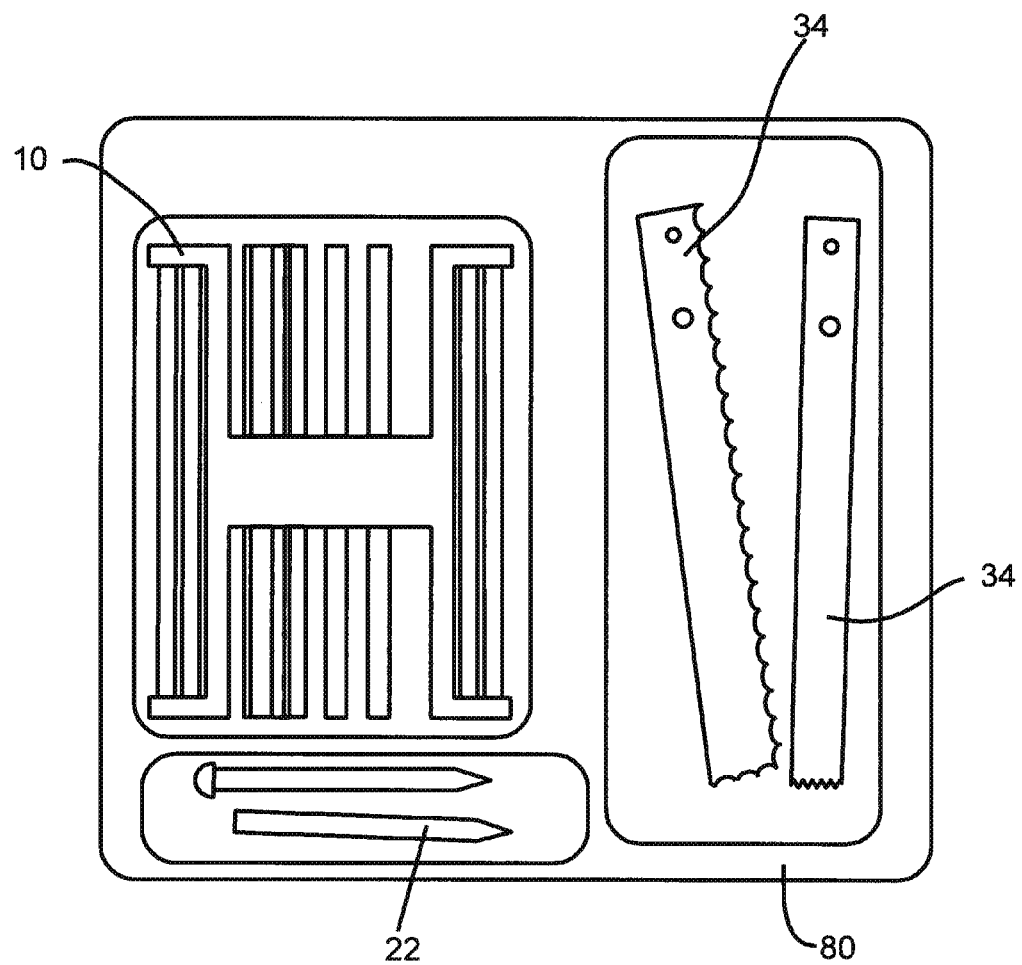
FIG. 16 is a top view of a kit of the invention.

Referring now to FIG. 16, a kit is provided which includes the following components: (a) the bone cutting fixture assembly 10, 10a-10e; (b) a selection, of saw blades 34; (c) a selection of fixing devices 22; and (d) a case 80 formed to organize and contain the components.

In an advantage, the fixture does not obscure the view of the surgeon to the cut Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone cutting fixture assembly for use as a guide for a cutting blade in shaping and preparing a bone to receive a component of a prosthesis, the fixture assembly comprising:
   a) a support structure providing a support surface extending along a support length;
   b) at least one fixing device extending beyond the support surface to enable the support structure to be affixed to a bone;
   c) at least one outrigger portion supported by the support structure and comprising a spike projecting in a downwardly direction sufficiently beyond the support surface to be anchorable into a bone;
   d) a first pair of side-by-side guide appendages, each having a first length extending from a first proximal portion supported by the support structure to a spaced apart first distal portion, wherein the first guide appendages have a circular cross-section perpendicular to the first length;
   e) a second pair of side-by-side guide appendages, each having a second length extending from a second proximal portion supported by the support structure to a spaced apart second distal portion, wherein the second guide appendages have a circular cross-section perpendicular to the second length;
   f) wherein the first and second guide appendages are separated from each other in the respective first and second pairs by respective first and second gaps of distances sufficient to enable the thickness of a cutting blade to pass between them; and
   g) wherein with respect to the support surface of the support structure, the first and second pairs of guide appendages are positioned one above the other such that an imaginary support plane bisects the first and second gaps to provide a cutting path at a desired angle for a cutting blade positioned between the first and second pairs of guide appendages.

2. The bone cutting fixture assembly of claim 1 wherein the at least one fixing device and the outrigger portion provide the support structure with spaced apart anchor points for securing the fixture to a bone.

3. The bone cutting fixture assembly of claim 2 wherein the support structure has a polygonal cross section perpendicular to the support length.

4. The bone cutting fixture assembly of claim 2 wherein the support structure has a trapezoidal cross section perpendicular to the support length.

5. The bone cutting fixture assembly of claim 2 wherein the support structure has a circular or elliptical cross section perpendicular to the support length.

6. The bone cutting fixture assembly of claim 1 wherein the support structure is made of a polymeric material.

7. The bone cutting fixture assembly of claim 1 wherein the support structure comprises at least one outrigger portion supported on each side of a central plane perpendicular to the support surface to thereby provide opposed anchor points.

8. The bone cutting fixture assembly of claim 1 wherein the first and second pairs of guide appendages extend from one side of the support structure.

9. The bone cutting fixture assembly of claim 1 wherein the fixture assembly comprises at least two spaced apart support structures, one of them supporting opposed proximal and distal portions of the first and second pairs of guide appendages.

10. The bone cutting fixture assembly of claim 1 wherein the fixture has a central anchor point.

11. The bone cutting fixture assembly of claim 1 wherein the fixture comprises at least the first and second pairs of guide appendages.

12. The bone cutting fixture assembly of claim 11 wherein there are a sufficient number of guide appendages to provide at least four cutting paths.

13. The bone cutting fixture assembly of claim 1 wherein the fixture comprises a sufficient number of pairs of guide appendages to provide at least two cutting paths.

14. The bone cutting fixture assembly of claim 1 wherein the guide appendages are slidable relative to the support structure.

15. A kit for use in knee surgery, the kit including the following components:
   a) at least one bone cutting fixture assembly of claim 1;
   b) a selection of saw blades;
   a selection of fixing devices; and
   d) a case formed to organize and contain the components.

16. The bone cutting fixture assembly of claim 1 wherein the outrigger portion also comprises a through bore disposed so that a removable bone spike is downwardly receivable in the bore.

17. The bone cutting fixture assembly of claim 16 wherein the bone spike is receivable in the bore at an angle with respect to the central plane perpendicular to the support surface.

18. The bone cutting fixture assembly of claim 1 wherein there are two outrigger portions extending from the support structure to provide respective anchor points in distal ends thereof.

19. A bone cutting fixture assembly, which comprises:
   a) a support structure having a support length and comprising at least one fixing device enabling the support structure to be affixed to a bone;
   b) a first pair of side-by-side guide appendages, each having a first length extending from a first proximal portion movably supported by the support structure to a spaced apart first distal portion, wherein the first guide appendages have a circular cross-section perpendicular to the first length;
   c) a second pair of side-by-side guide appendages, each having a second length extending from a second proximal portion movably supported by the support structure to a spaced apart second distal portion, wherein the second guide appendages have a circular cross-section perpendicular to the second length;
   d) wherein the first and second guide appendages are separated from each other in the respective first and second pairs by respective first and second gaps of distances sufficient to enable the thickness of a cutting blade to pass between them; and
   e) wherein with respect to a bottom surface of the support structure, the first and second pairs of guide appendages are positioned one above the other such that an imaginary support plane bisects the first and second gaps to provide a cutting path at a desired angle for a cutting blade positioned between the first and second pairs of guide appendages.

20. The bone cutting fixture assembly of claim 19 wherein the guide appendages are movable as being threadingly supported by the support structure.

21. The bone cutting fixture assembly of claim 20 wherein the threadingly supported guide appendages are translatable to extend from one or the other side of the support structure, or from both sides.

22. The bone cutting fixture assembly of claim 19 wherein the guide appendages are movable by means of a detent mechanism to extend from one or the other side of the support structure, or from both sides.

23. A bone cutting fixture assembly, which comprises:
   a) a support structure having a support length and comprising at least one fixing device enabling the support structure to be affixed to a bone;
   b) at least one outrigger portion extending from the support structure and comprising an anchor point;
   c) a first pair of side-by-side guide appendages, each having a first length extending from a first proximal portion movably supported by the support structure to a spaced apart first distal portion, wherein the first guide appendages have a circular cross-section perpendicular to the first length;
   d) a second pair of side-by-side guide appendages, each having a second length extending from a second proximal portion movably supported by the support structure to a spaced apart second distal portion, wherein the second guide appendages have a circular cross-section perpendicular to the second length;
   e) wherein the first and second guide appendages are separated from each other in the respective first and second pairs by respective first and second gaps of distances sufficient to enable the thickness of a cutting blade to pass between them; and
   f) wherein with respect to a bottom surface of the support structure, the first and second pairs of guide appendages are positioned one above the other such that an imaginary support plane bisects the first and second gaps to provide a cutting path at a desired angle for a cutting blade positioned between the first and second pairs of guide appendages.

24. The bone cutting fixture assembly of claim 23 wherein there are two outrigger portions extending from opposite sides of the support structure to opposing anchor points.

25. The bone cutting fixture assembly of claim 24 wherein the opposed outrigger portion are oriented perpendicular to the support length of the support structure.

26. The bone cutting fixture assembly of claim 23 wherein guide appendages are oriented perpendicular to the support length of the support structure.

27. The bone cutting fixture assembly of claim 24 wherein the outrigger portion has a circular cross-section perpendicular to its length and in conjunction with the first guide appendage provides the first gap disposed either vertically above or below the second pair of guide appendages providing the second gap such that the imaginary support plane bisects the first and second gaps to provide the cutting path at the desired angle for a cutting blade.

* * * * *